United States Patent [19]

Gschwend

[11] 3,939,271

[45] Feb. 17, 1976

[54] ANTIDEPRESSIVE AND ANTIANXIETY COMPOSITION COMPRISING 2-PYRAZOLYL-BENZOPHENONES

[75] Inventor: Heinz Werner Gschwend, New Providence, N.J.

[73] Assignee: Ciba-Geigy Corporation, Ardsley, N.Y.

[22] Filed: June 3, 1974

[21] Appl. No.: 475,475

[52] U.S. Cl............................ 424/273; 260/310 R
[51] Int. Cl.².................................... A61K 31/415
[58] Field of Search.................. 260/310 R; 424/273

[56] References Cited
UNITED STATES PATENTS

| 3,509,130 | 4/1970 | Bencze | 260/239 |
|---|---|---|---|
| 3,629,433 | 12/1971 | Gschwend | 424/273 |
| 3,752,892 | 8/1973 | Hoegerle et al. | 424/244 |

Primary Examiner—Donald B. Moyer
Attorney, Agent, or Firm—Joseph G. Kolodny; Theodore O. Groeger; John J. Maitner

[57] ABSTRACT

2-Pyrazolyl-benzophenones, e.g. those of the formula

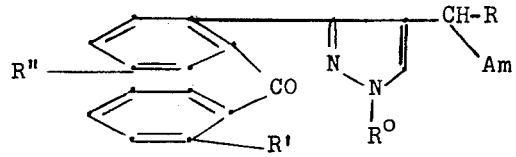

$R^o$ = H, alkyl, (HO, alkoxy, amino)- alkyl, aralkyl or aryl
R = H or alkyl
R',R'' = H, alkyl, alkoxy, halo or $CF_3$
Am = open or cyclic amino group corresponding ketals, carbinols, acyl derivatives or therapeutically useful acid addition salts thereof exhibit antianxiety and antidepressant effects.

4 Claims, No Drawings

ANTIDEPRESSIVE AND ANTIANXIETY COMPOSITION COMPRISING 2-PYRAZOLYL-BENZOPHENONES

SUMMARY OF THE INVENTION

The present invention concerns and has for its object the provision of new 2-(3- or 5-pyrazolyl)-benzophenones or -thiophenones, their ketals or carbinols corresponding to Formulae I and II

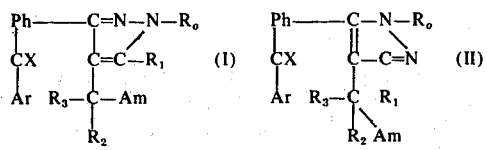

wherein Ph is a 1,2-phenylene radical, Ar is a monocyclic, carbocyclic aryl radical, $R_o$ is hydrogen, lower alkyl, (hydroxy, lower alkoxy or Am)-$C_mH_{2m}$ or Ar-$C_nH_{2n}$, Am is an open or cyclic amino group, $m$ is an integer from 1 to 7, $n$ such from 0 to 7, each of $R_1$, $R_2$ and $R_3$ is hydrogen or lower alkyl, and X is oxo, thio, or hydrogen and hydroxy or lower alkoxy; simple or mixed, open or cyclic lower alkyl or alkylene ketals thereof; or a lower alkanoyl, alkoxycarbonyl, AmCO or AmCS derivative of the compounds containing at least one hydrogen attached to oxygen or nitrogen; or a therapeutically useful acid addition salt thereof; as well as of corresponding pharmaceutical compositions and of methods for the preparation and application of these products, which are useful antianxiety and antidepressant agents.

DESCRIPTION OF THE PREFERRED EMBODIMENTS

The 1,2-phenylene radical Ph, as well as the aryl radical Ar, are unsubstituted or substituted by one or more than one, preferably by one or two, of the same or different substituents selected from the group consisting of lower alkyl, e.g. methyl, ethyl, n- or i-propyl or -butyl; etherified or esterified hydroxy, such as lower alkoxy, e.g. methoxy, ethoxy, n- or i-propoxy or -butoxy; or halo, e.g. fluoro, chloro or bromo; or trifluoromethyl. The term "lower", referred to above and hereinafter in connection with organic radicals or compounds respectively, defines such with up to 7, preferably up to 4, carbon atoms.

Preferred 1,2-phenylene radicals Ph are 1,2-phenylene, (lower alkyl)-1,2-phenylene, (lower alkoxy)-1,2-phenylene, (halo)1,2-phenylene or (trifluoromethyl)-1,2-phenylene and preferred aryl radicals Ar are phenyl, (lower alkyl)-phenyl, (lower alkoxy)-phenyl, mono- or di-(halo)-phenyl or (trifluoromethyl)-phenyl.

The radical $R_o$ preferably represents hydrogen, lower alkyl or Ar-$C_nH_{2n}$, wherein $n$ is an integer from 0 to 7, preferably 1 to 4. It may also represent (hydroxy, lower alkoxy or Am)-$C_mH_{2m}$ wherein m is an integer from 1 to 7 and Am is exemplified by animo, mono- or di-lower alkylamino, lower alkyleneimino or mono-aza-, oxa- or thiaalkyleneimino, wherein the additional nitrogen, oxygen or sulfur atom is separated from the imino-nitrogen by at least 2 carbon atoms, e.g. mono- or di-(methyl, ethyl, n- or i-propyl or -butyl)-amino; pyrrolidino, piperidino or hexamethyleneimino; piperazino, 4-(lower alkyl, e.g. methyl or ethyl)-piperazino; morpholino or thiamorpholino. Preferred amino groups Am are mono- or dilower alkylamino, pyrolidino, piperidino, piperazino, 4-(lower alkyl)-piperazino or morpholino.

The radicals $R_1$, $R_2$ and $R_3$ represent preferably a hydrogen atom, but also lower alkyl, above all methyl.

The ketals of said benzophenones or -thiophenones are either simple ketals or thioketals, or mixed ketals, containing oxygen and sulfur, and are derived either from lower alkanols or -thiols, or lower alkylene glycols or thioglycols respectively. Thus, X represents, for example, two members selected from methoxy, ethoxy, n- or i-propoxy, methyl- or ethylmercapto; or one member of 1,2-ethylenedioxy, 1,2- or 1,3-propylenedioxy or -thioxy.

Said acyl derivatives are either esters of said carbinols and/or amides of said primary or secondary Am-compounds, and the lower alkanoyl derivatives are exemplified by formyl, acetyl, propionyl or pivalyl derivatives; lower alkoxycarbonyl derivatives by methoxy-, ethoxy-, n- or i-propoxy- or -butoxycarbonyl derivatives; and AmCO and AmCS derivatives are preferably those of NH-compounds.

The compounds of the invention exhibit valuable pharmacological properties, for example, antianxiety and especially antidepressant effects, differing from those of imipramine. This can be demonstrated in animal tests, using advantageously mammals, such as mice, rats or monkeys, as test objects. The compounds of the invention can be applied to the animals enterally, e.g. orally, or parenterally, such as subcutaneously or intraperitoneally, e.g. in the form of aqueous solutions or starchy suspensions. The dosage may range between about 0.1 and 300 mg/kg/day, preferably between about 1 and 100 mg/kg/day, advantageously between about 2 and 20 mg/kg/day. An antidepressant effect is observed, for example, in the amphetamine interaction test (P. Carlton, Psychopharmacologia 1961, Vol. II, p. 364) performed with male albino rats, which are trained to press a bar every 30 seconds, in order to avoid an electric shock applied through the floor grid. In case the animals receive i.p. 0.25 mg/kg/day of amphetamine, their performing rate for avoiding said shock during a test period or about 4–5 hours is slightly higher than that of placebo (saline) treated animals. In case the animals receive the compounds of the invention (or imipramine for control purposes) in the above-mentioned doses, preferably at 5 or 10 mg/kg/day i.p. and about 45 minutes later the amphetamine, their rate of avoiding the shocks is highest, as compared with that of rats receiving (a) saline alone, (b) saline and amphetamine, or (c) the compounds or the invention and saline. In addition the compounds of the invention exhibit antianxiety effects in rats or squirrel monkeys, advantageously at dosages between about 2 and 20 mg/kg/day. Accordingly, they reduce acquired fear or anxiety associated with a psychological conflict. It is established by simultaneously rewarding with food and punishing with electric shock all lever-pressing responses of the animals made in the presence of a discriminative tone stimulus. For example, rats first learn to press a lever to obtain a milk reward, which is delivered on the average of once per 2 minutes. After this schedule, which lasts 15 minutes, a tone stimulus of 3 minute duration is presented. This stimulus signals a change from a variable interval schedule of reinforcement, to a continuous reinforcement schedule (CRF). During the CRF schedule, all lever responses not only produce milk rewards but also an electric shock to the animals' feet. During the period in which a shock accompanies the food reward, the tone stimulus produces a suppression of all lever pressing responses. Thus, for example, administration of 5-chloro-2(1-methyl-4-aminomethyl-5-pyrazolyl)-2'-fluorobenzophenone monophosphate, a characteristic compound of the invention applied at about 5 mg/kg/day intraperitoneally to rats or orally to squirrel monkeys, reinstate these responses, indicating that the animals tolerate more shocks in obtaining the food reinforcement. Accordingly, the compounds of the invention are especially useful in combatting depression and axiety. Moreover, they are also valuable intermediates in the preparation of other useful products, especially of pharmacologically active compounds.

Particularly useful are compounds of Formulae I and II, in which Ph is 1,2-phenylene, (lower alkyl)-1,2-phenylene, (lower alkoxy)-1,2-phenylene, (halo)-1,2-phenylene or (trifluoromethyl)1,2-phenylene, Ar is H-Ph, $R_o$ is hydrogen, lower alkyl, (hydroxy, lower alkoxy or Am)-$C_mH_{2m}$, or Ar-$C_nH_{2n}$, Am is amino, mono- or di-lower alkylamino, or five to seven ring-membered lower alkyleneimino, $m$ is an integer from 2 to 4, and $n$ such from 0 to 4, each of $R_1$, $R_2$ and $R_3$ is hydrogen or lower alkyl and X is oxo, thio, or hydrogen and hydroxy or lower alkoxy, or the simple or mixed, open or cyclic lower alkyl or alkylene ketals thereof, or lower alkanoyl, alkoxy-carbonyl, AmCO or AmCS derivatives of the compounds containing at least one hydrogen attached or oxygen or nitrogen, or a therapeutically useful acid addition salt thereof.

Preferred compounds of the invention are those of Formula I and II, wherein Ph is 1,2-phenylene, (alkyl)-1,2-phenylene or (halo)-1,2-phenylene, Ar is H-Ph, $R_o$ is hydrogen, alkyl, 2- or 3(hydroxy or dialkylamino)-(ethyl or propyl) or H-Ph-methyl, each of $R_1$, $R_2$ and $R_3$ is hydrogen or methyl, the group Am is amino or dialkylamino, X is oxo, thio, two alkoxy groups, one alkoxy and alkylmercapto group, or ethylenedioxy, or an alkanoyl derivative of the compounds containing at least one hydrogen attached to oxygen or nitrogen, in which compounds alkyl, alkanoyl, alkoxy or alkylmercapto has up to 4 carbon atoms, or a therapeutically useful acid addition salt thereof.

Outstanding are the compounds of Formulae III and IV

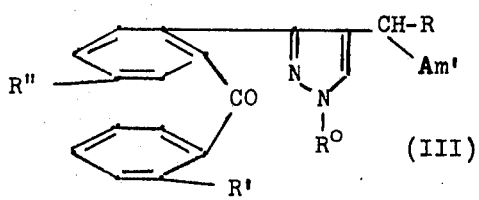

(III)

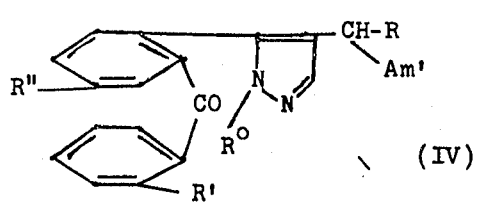

(IV)

wherein R is hydrogen or methyl, $R^o$ is hydrogen, methyl, ethyl, n- or i-propyl, n-, i- or t-butyl, 2- or 3-(hydroxy, dimethylamino-or diethylamino)-(ethyl or propyl) or benzyl, each of R' and R'' is hydrogen, methyl, fluoro or chloro and Am' is amino, dimethylamino or diethylamino, the methyl or ethylene ketal or thioketal, or a therapeutically useful addition salt thereof.

The compounds of this invention are prepared according to conventional methods, for example by converting in compounds of Formulae Va or b

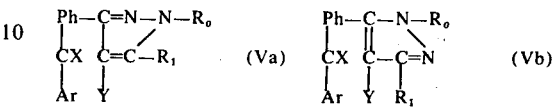

in which Y is a substituent capable of being converted into $R_2$, $R_3$-'C-Am, Y into said α-aminoalkyl group and, if desired, converting any resulting compound into another compound of the invention.

The substituent Y is, for example, a reactively esterified α-hydroxy-alkyl group, preferably such derived from a strong inorganic metalloidic acid, particularly a hydrohalic acid, e.g. hydrochloric or hydrobromic acid or sulfuric acid, or an organic sulfonic acid, such as a lower alkane or benzene sulfonic acid, e.g. methane, ethane, benzene or p-toluene sulfonic acid, or an α-phosphonium-alkyl group, e.g. an α-triphenyl-phosphonium halidealkyl group. Said groups Y are converted into α-Am-alkyl by condensation with H-Am or an alkali metal, e.g. sodium salt thereof.

Another substituent Y is, for example, an α-(nitro, oximino or imino)-alkyl group, or preferably a cyano or carbamoyl group, e.g. CO-Am, which groups can be converted into α-Am-alkyl by reduction. The above nitro compounds, nitriles or amides are advantageously reduced with the use of simple or complex light metal hydrides, such as boron hydride or alkali metal aluminum hydrides, e.g. lithium aluminum hydride. The above oximes or Schiff's bases, i.e. said α-oximino- or iminoalkyl compounds, as well as the α-nitroalkyl or cyano compounds, can also be reduced with catalytically activated or nascent hydrogen, such as hydrogen in the presence of nickel, platinum or preferably palladium catalysts, or generated electrolytically or by the action of metals on compounds with active hydrogen, such as acids or alcohols, e.g. zinc or iron and inorganic or organic acids, such as hydrohalic or lower alkanoic acids, or sodium or aluminum or their amalgams and lower alkanols.

Another process for the preparation of the compounds of Formulae I and II consists in hydrolyzing compounds of Formulae Vc or d

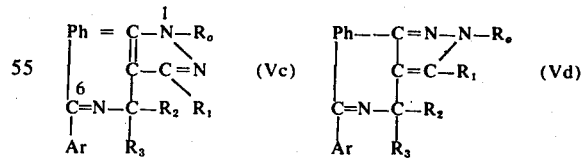

and, if desired, converting any resulting product into another compound of the invention.

Hydrolysis is advantageously performed under mildly acidic conditions, e.g. in the presence of aqueous and-/or alkanolic acids, e.g. said metalloidic acids, or the therapeutically useful acids listed below.

The carbinols of the invention (X=H+OH) are obtained from the ketones (X=O) by reduction as shown for the amides, advantageously with complex borohydrides, e.g. sodium boro- or lithium borohydride, or aluminum hydrides, e.g. lithium aluminum hydride in protic or non-protic solvents.

Another process for the preparation of the compounds of Formulae I and II consist in condensing a ketal or ether of Formula Ve

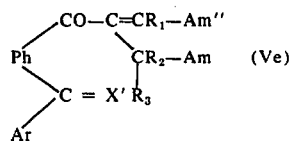

wherein X' is said X different from O, S or H+OH and Am'' is said Am different from a primary or secondary amino group, with $R_1$—NH— $NH_2$ and if desired, converting any resulting compound into another compound of the invention.

The substituent X' is preferably lower alkoxy and alkylmercapto and Am'' preferably di-lower alkylamino. Said condensation is advantageously performed at elevated temperatures, for example between about 30 and 150° and in the presence or absence of a lower alkanol.

The compounds thus obtained can be converted into each other according to conventional methods. For example, resulting compounds containing at least one hydrogen atom attached to oxygen or nitrogen can be acylated, for example, with the use of reactive functional derivatives of the corresponding acids, such as halides or anhydrides thereof, e.g. acetyl or propionyl chloride, lower alkyl chloroformates, carbamoyl or thiocarbamoyl chlorides; acetic anhydride, ketene, isocyanates or isothiocyanates. Said primary or secondary amines can also be reacted with reactives esters of the respective alcohols, preferably derived from hydrohalic, aliphatic or aromatic sulfonic acids, e.g. lower alkyl or aralkyl chlorides, bromides, iodides; alkane- or benzenesulfonates, e.g. the mesylate or tosylate, or with correspodning aldehydes or ketones and reducing agents, e.g. formic acid, in order to obtain sec. or tert. amines respectively. Resulting ketals can also be converted into the ketone or thioketones, for example, by treating them with acidic agents, such as the above inorganic or organic acids. Finally, a resulting base can be converted into a corresponding acid addition salt, preferably with the use of a therapeutically useful acid or anion exchange preparation, or resulting salts can be converted into the corresponding free bases, for example, with the use of a base, such as a metal hydroxide, basic salt, ammonia, amine or cation exchange preparation, e.g. an alkali metal hydroxide or carbonate. Said acid addition salts are preferably such of therapeutically useful inorganic acids, such as strong metalloidic acids, for example hydrohalic, e.g. hydrochloric or hydrobromic acid; sulfur, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyroracemic, phenylacetic, benzoic 4-aminobenzoic, anthranilic, 4-hydroxybenzoic, salicylic, 4-aminosalicylic, embonic, nictinic; methanesulfonic, ethanesulfonic, hydroxyethanesulfonic, ethylenesulfonic, halogen-benzenesulfonic, toluenesulfonic, naphthalenesulfonic or sulfanilic acid.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances. Resulting mixtures of isomers can be separated into the single isomers by methods in themselves known, e.g. by fractional distillation, crystallization and/or chromatography.

The invention further includes any variant of the present process in which an intermediate product obtainable at any stage of the process is used as starting material and any remaining steps are carried out, or the process is discontinued at any stage thereof, or in which the starting materials are formed under the reaction conditions, or in which the reaction components are used in the form of their salts. Mainly those starting materials should be used in the reactions of the invention that lead to the formation of those compounds indicated above as being especially valuable.

The starting material Vc to d is new and is considered as additional subject matter of the present invention. It is prepared according to the following formula scheme, which is illustrated by the examples herein:

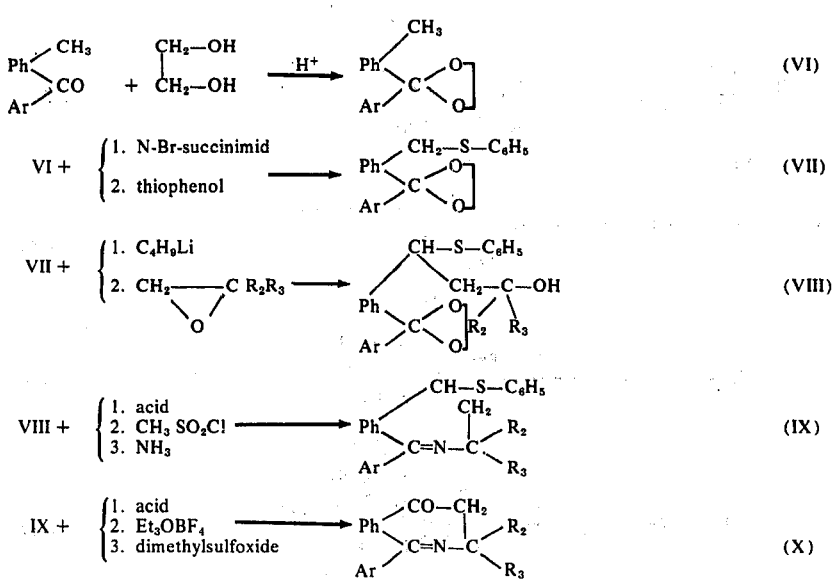

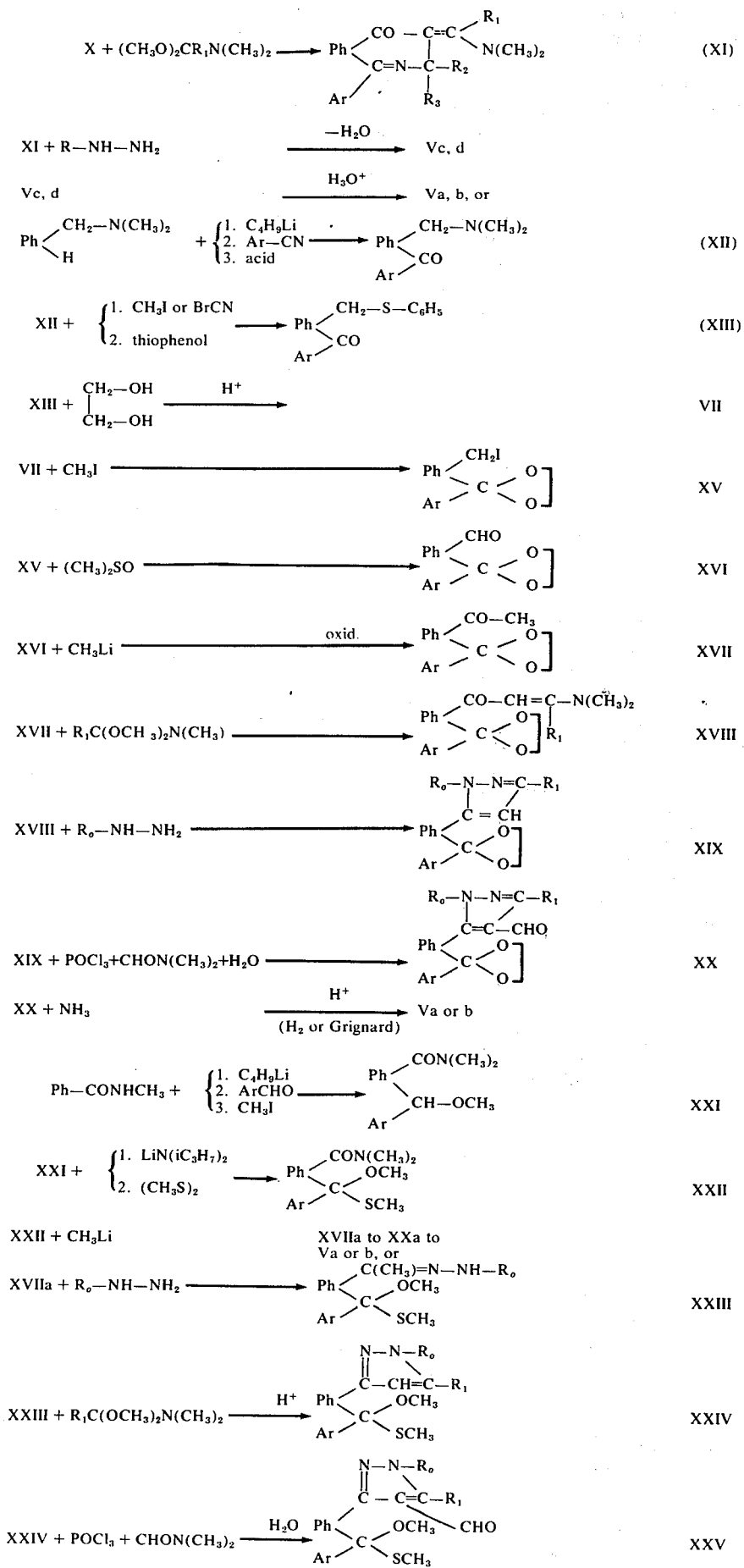

XXV + NH₂OCH₃ ⟶ Va, or

XXII + CH₂=CHMgBr ⟶ 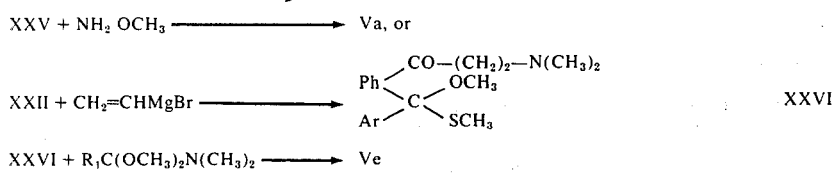 XXVI

XXVI + R₁C(OCH₃)₂N(CH₃)₂ ⟶ Ve

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose, and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylecellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promoters, salts for regulating the osmotic pressure and/or buffers. They may also contain other therapeutically valuable substances. Said pharmaceutical compositions are prepared according to conventional mixing, granulating or coating methods respectively and contain about 0.1 to 75%, preferably about 1 to 50% of the active ingredient.

The following examples, illustrating the invention, are not to be construed as being limitations thereon. Temperatures are given in degrees Centigrade and all parts wherever given are parts by weight.

EXAMPLE 1

The mixture of 130 mg of 5-chloro-2-(1-methyl-4-methoxyiminomethyl-5-pyrazolyl-2'-fluorobenzophenone ethylene ketal, 25 ml of diethyl ether and 100 mg of lithium alluminum hydride is stirred at room temperature for 16 hours. Thereupon 0.1 ml of water, 0.1 ml of 15% aqueous sodium hydroxide and 0.3 ml of water are added, the mixture filtered and the filtrate extracted with N hydrochloric acid. The acidic layer is separated, made basic with 2N aqueous sodium hydroxide, extracted with methylene chloride, the extract dried and evaporated, to yield the 5-chloro-2-(1-methyl-4-aminomethyl-5-pyrazolyl)-2'-fluorobenzophenone ethylene ketal of the Formula IV, wherein R=H, Am'=NH₂, R⁰=CH₃, R'=F and R''=Cl, showing in the NMR-spectrum a singlet at δ=3.03 and a triplet at δ=8.0 ppm.

The mixture of 100 mg thereof, 10 ml of dioxane and 10 ml of 2N hydrochloric acid is refluxed for 1 hour under nitrogen and the dioxane evaporated. The aqueous solution is cooled, admixed to methylene chloride, made basic with 2N aqueous sodium hydroxide and extracted with diethyl ether. The extract is dried, filtered into the solution of 50 mg of phosphoric acid in 1 ml of ethanol and the precipitate filtered off, to yield the 5-chloro-2-(1-methyl-4-aminomethyl-5-pyrazolyl)-2'-fluorobenzophenone monophosphate melting at 180°.

The starting material is obtained as follows: The solution of 10 g of 5-chloro-2'-fluoro-2-phenylmercaptomethyl-benzophenone ethylene ketal (Example 2) in 50 ml of methyl iodide is refluxed under nitrogen for 5 days. It is evaporated and the formed methyl phenyl thioether distilled off at 60°/0.1 mm Hg, to yield the 5-chloro-2'-fluoro-2-iodomethyl-benzophenone ethylene ketal.

The mixture of 9.6 g thereof, 5 g sodium bicarbonate and 50 ml of dimethylsufoxide is stirred for 20 minutes at 110°, cooled and poured onto ice. The mixture is extracted with diethyl ether, the extract washed with water and saturated aqueous sodium chloride, dried, evaporated and the residue recrystallized from diethyl ether-hexane, to yield the 5-chloro-2'-fluoro-2-formyl-benzophenone ethylene ketal melting at 103°–105°.

To the solution of 1.6 g thereof in 60 ml of diethyl ether, 3 ml of 2.3 molar methyl lithium in diethyl ether are added while stirring and cooling with ice. After 5 minutes 20 ml of water are added cauteously, the organic layer separated, washed with saturated aqueous sodium chloride, dried and evaporated, to yield the 5-chloro-2'-fluoro-2-(1-hydroxy-ethyl)-benzophenone ethylene ketal showing in the NMR-spectrum a doublet a δ=1.1 ppm (in deuterochloroform).

To the solution of 1.8 g thereof in 100 ml or diethyl ether, 25 ml of the solution (obtained from 100 g of sodium dichromate dihydrate, 300 ml of water, 136 ml of concentrated sulfuric acid and diluting it with water to 500 ml) are added while stirring. After 40 minutes the mixture is poured on ice, the organic phase separated and washed with aqeuous sodium bisulfite, water, aqeuous sodium bicarbonate and saturated aqueous sodium chloride. It is dried and evaporated, to yield the 2-acetyl-5-chloro- 2'-fluorobenzophenone ethylene ketal showing in the NMR spectrum a singlet at δ=2.4 ppm.

The mixture of 1.1 g thereof and 7 ml of dimethyl formamide dimethylacetal is refluxed for 16 hours and evaporated under reduced pressure, to yield the 5-chloro-2-(3-dimethylaminoacryloyl)2'-fluoro-benzophenone ethylene ketal showing in the NMR-spectrum a broad singlet at δ=2.7 ppm.

The mixture of 1.3 g thereof, 0.3 g of methylhydrazine and 25 ml of ethanol is refluxed for 7 hours under nitrogen and evaporated. The residue is chromatographed on silica gel and the column eluted first with benzene, then diethyl ether and the ether eluate collected, to yield the 5-chloro-2'-fluoro-2-(1-methyl-5-pyrazolyl)-benzophenone ethylene ketal showing in the NMR-spectrum a singlet at δ=3.1 and a doublet at δ=5.95 ppm.

The solution of 650 mg thereof in 2.7 ml of ethylene dichloride is added dropwise to the complex, prepared from 265 mg of dimethylformamide and 555 mg of phosphorus oxychloride, while cooling with ice, and dissolved in 1.8 ml of ethylene dichloride, while stirring and the mixture is refluxed for 2 hours under nitrogen. After cooling the solution of 2.45 g of sodium acetate trihydrate in 3.6 ml of water is added and the mixture refluxed for 15 minutes. It is diluted with methylene chloride and water, the organic layer separated and dried, to yield the 5-chloro-2'-fluoro-2-(1-methyl-4-formyl-5-pyrazolyl)-benzophenone ethylene ketal, showing in the NMR-spectrum a band at δ=9.13 ppm.

The mixture of 660 mg thereof, 3 ml of pyridine and 170 mg of O-methyl-hydroxylamine hydrochloride is stirred for 16 hours at room temperature and evaporated under reduced pressure. The residue is taken up in chloroform and the solution filtered through a short column of silica gel, to yield the desired methoxime.

EXAMPLE 2

The mixture of 3.25 g of 8-chloro-6-(2-fluorophenyl)-1-methyl-1H,4H-pyrazolo-[4,3-d](2)benzazepine, 100 ml of 0.5N sulfuric acid and 15 ml of ethanol is stirred under nitrogen at room temperature for 2 days. The resulting solution is cooled to 0°, transferred into a separatory funnel, made basic with ice-cold 30% aqueous sodium hydroxide and quickly extracted with diethyl ether. The extract is dried filtered into the mixture of 1.2 g of 85% phosphoric acid and 50 ml ethanol and the precipitate collected, to yield the monophosphate identical with that of Example 1, m.p. 180°.

Analogously the 5-chloro-2-(1-methyl-4-aminomethyl-5-pyrazolyl)-benzophenone monooxalate is obtained, melting at 163°–165°.

The starting material is prepared as follows: The solution of 141 g of α,p-dichlorotoluene in 200 ml tetrahydrofuran is added dropwise to an ice-cold saturated solution of dimethylamine in 1 liter of tetrahydrofuran and the mixture stirred for 2 days at 25°. It is diluted with diethyl ether, washed with 2N aqueous sodium hydroxide, the organic layer dried, evaporated, the residue distilled and the fraction boiling at 106°/12 mm Hg collected, to yield the N,N-dimethyl-4-chlorobenzylamine.

To the solution of 81.6 g thereof in 1.5 lt of diethyl ether 360 ml of 1.6 molar n-butyl lithium in hexane are added dropwise while stirring at 0°–5° under nitrogen. After 3 hours the solution of 58 g of 2-fluorobenzonitrile in 1.5 lt of diethyl ether is added dropwise while stirring, the mixture refluxed for 3 hours and stirred at room temperature for 16 hours. Thereupon crushed ice and 265 ml of 5N hydrochloric acid are added, the mixture refluxed for ½ hour, cooled and the aqueous layer separated. It is made basic with 30% aqueous sodium hydroxide, extracted with methylene chloride, the extract dried, evaporated and the residue dried in a high vacuum at 100°, to yield the 5-chloro-2'-fluoro-2-dimethylaminomethyl-benzophenone melting at 91°–92°.

To the solution of 138 g thereof in 3.2 lt of methylene chloride, that of 55 g of cyanogen bromide in 300 ml of methylene chloride is added dropwise while stirring and cooling with ice. After stirring overnight, the mixture is evaporated under reduced pressure at 40°. The residue is taken up in 2.4 lt of methanol, 56.8 ml of thiophenol are added, followed by 596 ml of N methanolic sodium hydroxide, the mixture stirred for 2 hours at 0° and overnight at room temperature. It is cooled again, filtered and the residue washed with methanol, to yield the 5-chloro-2'-fluoro-2-phenylmercaptomethyl-benzophenone melting at 81°–82°.

The mixture of 144.6 g thereof, 386 g of p-toluenesulfonic acid, 800 ml of ethylene glycol and 3 lt of benzene is refluxed at the water separator for 19 days and evaporated under reduced pressure, to yield the corresponding ethylene ketal melting at 69°.

To the solution of 24.2 g thereof in 285 ml of dry tetrahydrofuran, 46.2 ml of 1.6 molar n-butyl lithium in hexane are added while stirring under nitrogen at −67° to −70°. After one hour 100 ml of 6 molar ethyleneoxide in tetrahydrofruan are added during 5 minutes, the temperature allowed to rise to −35° and the mixture stirred for two hours at room temperature. It is evaporated under reduced pressure, the residue taken up in 165 ml of dioxane, 165 ml of 2N hydrochloric acid are added and the mixture refluxed for 1 hour. It is concentrated under reduced pressure to about half its volume, the concentrate extracted with methylene chloride, the extract dried and evaporated, to yield the 5-chloro-2-(3-phenylmercaptopropyl)-1-phenylmetcaptopropyl)-2'-fluorobenzophenone.

To the mixture of 26 g thereof, 16 ml of N,N-diisopropylethylamine and 360 ml of diethyl ether, 9.2 ml of methanesulfonyl chloride are added dropwise while stirring at 0°. After 16 hours the mixture is washed with ice cold 5% hydrochloric acid, ice water and ice cold aqueous sodium carbonate, dried and evaporated under reduced pressure and below 30°. The residual methanesulfonate is taken up in 220 ml of methanol, saturated with ammonia, while stirring and after two hours the solution is again saturated with ammonia. It is allowed to stand at room temperature for 27 days, the precipitate (B) formed filtered off and the filtrate evaporated. The residue is taken up in diethyl ether, the solution extracted with 2N sulfuric acid, the aqueous solution made basic with 30% aqueous sodium hydroxide and extracted with methylene chloride. The extract is dried, evaporated, the residue combined with (B) and recrystallized from acetone, acidified with ethereal hydrogen chloride to yield the 8-chloro-1-(2-fluorophenyl)5-phenylmercapto-3,4-dihydro-2-benzazepine hydrochloride melting at 184°–185°.

The solution of 34.8 g thereof in 340 ml of methylene chloride is combined with 300 ml of 1.25 molar triethyloxonium tetrafluoroborate in methylene chloride while stirring under nitrogen. After 68 hours the mixture is evaporated under reduced pressure, the residue dissolved in 500 ml or dimethylsulfoxide and the solution stirred under nitrogen at 55° for 6 hours. It is evaporated under reduced pressure, the residue taken up in diethyl ether, the solution washed with water and extracted with 5% hydrochloric acid. The pH of the acidic solution is adjusted to 8 with sodium carbonate and the mixture extracted with diethyl ether. The extract is washed with water and saturated aqueous sodium chloride, the washings re-extracted with diethyl ether, the combined extracts dried, evaporated and the residue recrystallized from diethyl ether with the aid of charcoal, to yield the 8-chloro-1-(2-fluorophenyl)-3,4-dihydro-2-benzazepin-5-one melting at 107°–109°.

The mixture of 3.4 g thereof and 275 ml of dimethylformamide-dimethylacetal is refluxed for 75 minutes and the excessive reagent removed under reduced pressure at a temperature not exceeding 135°. The residue is crystallized from diethyl ether, to yield the 8-chloro-4-dimethylamino-methylidene-1-(2-fluorophenyl)-3,4-dihydro-2-benzazepin-5-one melting at 224°–226°.

2 g thereof are added to the solution of 0.7 g of methylhydrazine in 100 ml of ethanol, the mixture refluxed for 45 minutes and evaporated under reduced pressure. The residue is recrystallized from ethyl acetate-hexane, to yield the 8-chloro-6-(2-fluorophenyl)-10a-hydroxy-1-methyl-3a,10a-dihydro-1H,4H-pyrazolo[4,3-d](2)benzazepine melting at 114°–115°.

The solution of 1.74 g thereof in 60 ml of chloroform is stirred with 100 ml of 0.1 N hydrochloric acid for 15 minutes, the pH of the aqueous phase adjusted to 8 with aqueous sodium carbonate and the mixture again stirred for 5 minutes. The organic layer is separated, dried, evaporated and the residue recrystallized from diethyl ether-hexane, to yield the 8-chloro-6-(2-fluorophenyl)1-methyl-1H,4H-pyrazolo [4,3-d](2)benzazepine melting at 128°–130°. The corresponding dihydrochloride melts at 190° with decomposition.

EXAMPLE 3

The solution of 13 g of 8-chloro-6-(2-fluorophenyl)-1-methyl-1H,4H-pyrazolo [4,3-d](2) benzazepine in 50.7 g of formic acid and 31.2 ml of 37% aqueous formaldehyde is refluxed for 10 hours. It is evaporated under reduced pressure, the residue taken up in methylene chloride and poured on ice and excess 30% aqueous sodium hydroxide. Separation of the organic layer, drying and removal of the solvent results in a solid product which, on neutralization of an acetone solution with ethereal hydrogen chloride, yields the 5-chloro-2-(1-methyl-4-dimethylaminomethyl-5-pyrazolyl)2'-fluorobenzophenone hydrochloride melting at 225°–227°.

EXAMPLE 4

The solution of 1.86 g of 5-chloro-2-(1-methyl-4-dimethylaminomethyl-5-pyrazolyl)-2'-fluorobenzophenone in 100 ml of ethanol is stirred for 2½ hours at room temperature with 500 mg sodium borohydride. It is evaporated under reduced pressure and the residue shaken with methylene chloride and 5% aqueous sodium hydroxide. After drying the organic layer and removal of the solvent, the residue is crystallized from diethyl ether-hexane, to yield the α-[5-chloro-2-(1-methyl-4-dimethylaminomethyl-5-pyrazolyl)-phenyl]-2fluorobenzyl alcohol melting at 125° to 127°; the hydrochloride thereof melts at 225°–230°.

EXAMPLE 5

Preparation of 10,000 tablets each containing 25 mg of the active ingredient:

Formula:

| | |
|---|---|
| 5-chloro-2-(1-methyl-4-aminomethyl-5-pyrazolyl)-2'-fluorobenzophenone mono-phosphate | 250.00 g |
| Lactose | 1,956.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which granulated, if necessary, with an additional amount of water. The granulate is dried overnight at 35°, broken on a screen with 1.2 mm openings and compressed into tablets using concave punches with 7.1 mm diameter, uppers bisected.

Preparation of 10,000 capsules each containing 10 mg of the active ingredient:

Formula:

| | |
|---|---|
| 5-chloro-2-(1-methyl-4-aminomethyl-5-pyrazolyl)-2'-fluorobenzophenone mono-phosphate | 500.0 g |
| Lactose | 2,350.0 g |
| Talcum powder | 150.0 g |

Procedure:

All the powders are passed through a screen with openings of 0.6 mm. Then the drug substance is placed in a suitable mixer and mixed first with the talcum, then with the lactose until homogenous. No. 2 capsules are filled with 300 ml of the mixture, using a capsule filling machine.

I claim:

1. An antidepressive and antianxiety pharmaceutical composition comprising a antidepressively or anxiolytic effective amount of a compound corresponding to the formulae

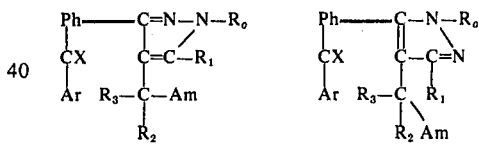

wherein Ar is unsubstituted phenylene, or phenyl substituted by one or two, of the same or different substituents selected from the group consisting of lower alkyl, lower alkoxy, halo or trifluoromethyl, Ph is 1,2-phenylene substituted by one or two halogen atoms, $R_o$ is hydrogen, lower alkyl, (hydroxy, lower alkoxy or Am)$C_mH_{2m}$ or Ar-$C_nH_{2n}$, wherein Am is amino, mono- or di-lower alkylamino, lower alkyleneimino or mono-aza-, oxa- or thia-alkyleneimino, wherein the additional nitrogen, oxygen or sulfur atom is separated from the iminonitrogen by at least 2 carbon atoms, $m$ is an integer from 1 to 7, $n$ such from 0 to 7, each of $R_1$, $R_2$ and $R_3$ is hydrogen or lower alkyl, and X is oxo, thio or hydrogen and hydroxy or lower alkoxy, simple or mixed, open or cyclic lower alkyl or alkylene ketals thereof; or a lower alkanoyl, alkoxycarbonyl, AmCO or AmCS derivative of the compounds containing at least one hydrogen attached to oxygen or nitrogen; or a therapeutically useful acid addition salt thereof, together with an enterally or parenterally applicable pharmaceutical excipient.

2. A composition as claimed in claim 1, wherein the effective compound corresponds to the formulae

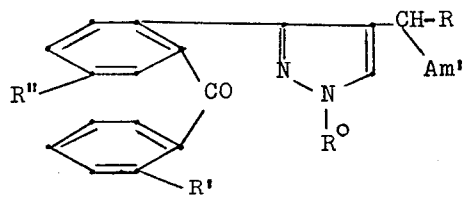
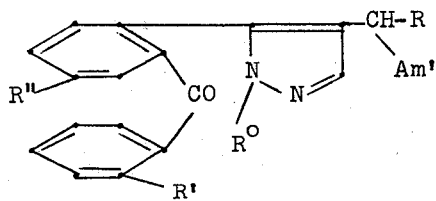

wherein R is hydrogen or methyl, R⁰ is hydrogen, methyl, ethyl, n- or i-propyl, n-, i- or t-butyl, 2- or 3-(hydroxy, dimethylamino-or diethylamino)-(ethyl or propyl) or benzyl, R' is hydrogen, methyl, fluoro or chloro, R'' is chloro and Am' is amino, dimethylamino or diethylamino, the methyl or ethylene ketal or thioketal, or a therapeutically useful acid addition salt thereof.

3. A composition as claimed in claim 1, wherein the effective compound is the 5-chloro-2-(1-methyl-4-aminomethyl-5-pyrazolyl)-2'-fluorobenzophenone or a therapeutically useful acid addition salt thereof.

4. A method of treating depression and anxiety, which consists in administering to a host suffering from depression and anxiety a composition as claimed in claim 1.

* * * * *